United States Patent
Wright et al.

(10) Patent No.: US 9,110,039 B2
(45) Date of Patent: Aug. 18, 2015

(54) AUTO-FOCUS SYSTEM AND METHODS FOR DIE-TO-DIE INSPECTION

(71) Applicant: KLA-Tencor Corporation, Milpitas, CA (US)

(72) Inventors: Michael J. Wright, San Carlos, CA (US); Zhengcheng Lin, San Jose, CA (US); Wilfred L. Ghonsalves, San Jose, CA (US); Daniel L. Belin, San Jose, CA (US); Weston L. Sousa, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/336,875

(22) Filed: Jul. 21, 2014

(65) Prior Publication Data

US 2015/0029499 A1     Jan. 29, 2015

Related U.S. Application Data

(60) Provisional application No. 61/858,308, filed on Jul. 25, 2013.

(51) Int. Cl.
*G01N 21/00* (2006.01)
*G01N 21/956* (2006.01)
*G01N 21/95* (2006.01)

(52) U.S. Cl.
CPC .......... *G01N 21/956* (2013.01); *G01N 21/9501* (2013.01); *G01N 2021/95676* (2013.01)

(58) Field of Classification Search
USPC ................ 356/600–614, 237.1–237.6, 239.3, 356/239.7, 239.8
See application file for complete search history.

(56) References Cited

U.S. PATENT DOCUMENTS

| 7,835,015 B1 | 11/2010 | Wright et al. |
| 2009/0009741 A1 | 1/2009 | Okita et al. |
| 2010/0171947 A1 | 7/2010 | Yoshino |
| 2011/0280469 A1 | 11/2011 | Lee |

FOREIGN PATENT DOCUMENTS

| JP | 2011-009554 A | 1/2011 |
| KR | 10-1255923 B1 | 4/2013 |

OTHER PUBLICATIONS

"Int'l Application Serial No. PCT/US2014/047880, Search Report and Written Opinion mailed Nov. 15, 2014", 11 pgs.

*Primary Examiner* — Tri T Ton
(74) *Attorney, Agent, or Firm* — Kwan & Olynick LLP

(57) ABSTRACT

Disclosed are methods and apparatus for detecting defects in a semiconductor sample having a plurality of identically designed areas. An inspection tool is used to construct an initial focus trajectory for a first swath of the sample. The inspection tool is then used to scan the first swath by following the initial focus trajectory for the first swath while collecting autofocus data. A z offset measurement vector for each identically designed area in the first swath is generated based on the autofocus data. A corrected z offset vector is constructed for inspection of the first swath with the inspection tool. Constructing the corrected z offset vector is based on combining the z offset measurement vectors for two or more of the identically designed areas in the first swath so that the corrected z offset vector specifies a same z offset for each set of same positions in the two or more identically designed areas.

20 Claims, 10 Drawing Sheets

AUTO-FOCUS SYSTEM AND METHODS FOR DIE-TO-DIE INSPECTION

CROSS-REFERENCE TO RELATED APPLICATION

This application claims priority to U.S. Provisional Patent Application No. 61/858,308, filed 25 Jul. 2013, which application is incorporated herein by reference in its entirety for all purposes.

TECHNICAL FIELD OF THE INVENTION

The invention generally relates to the field of wafer and reticle inspection systems. More particularly the present invention relates to auto-focusing techniques for use in die-to-die inspection.

BACKGROUND

Generally, the industry of semiconductor manufacturing involves highly complex techniques for fabricating integrating circuits using semiconductor materials that are layered and patterned onto a substrate, such as silicon. An integrated circuit is typically fabricated from a plurality of reticles. Generation of reticles and subsequent optical inspection of such reticles have become standard steps in the production of semiconductors. The fabrication of semiconductor devices, such as logic and memory devices, typically includes processing a semiconductor wafer using a large number of semiconductor fabrication processes with multiple reticles to form various features and multiple levels of the semiconductor devices. Multiple semiconductor devices may be fabricated in an arrangement on a single semiconductor wafer and then separated into individual semiconductor devices.

If there are defects on the reticle or wafer, the resulting semiconductor devices may not function properly. Accordingly, various inspection system features and techniques have been employed to improve defect detection sensitivity for both reticles and wafers. One factor that affects accurate defect detection is the particular technique employed to control focus of the inspection tool. Such focus control can be referred to as autofocus.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method for detecting defects in a semiconductor sample having a plurality of identically designed areas is disclosed. An inspection tool is used to construct an initial focus trajectory for a first swath of the sample. The inspection tool is then used to scan the first swath by following the initial focus trajectory for the first swath while collecting autofocus data. A z offset measurement vector for each identically designed area in the first swath is generated based on the autofocus data. A corrected z offset vector is constructed for inspection of the first swath with the inspection tool. Constructing the corrected z offset vector is based on combining the z offset measurement vectors for two or more of the identically designed areas in the first swath so that the corrected z offset vector specifies a same z offset for each set of same positions in the two or more identically designed areas.

In a specific implementation, an initial focus map that specifies z offsets for a plurality of swaths that are located at a plurality of different y positions of the sample is constructed, and the initial focus trajectory for the first swath is based on the initial focus map. In a further aspect, the y positions of the swaths for which the initial focus map specifies z offsets do not include the first swath's y position, and the initial focus trajectory for the first swath is constructed by interpolation between two initial focus trajectories, which have first and second y positions between which the swath's y position is located and that are specified by the initial focus map.

In another embodiment, the initial focus trajectory for the first swath is constructed by (i) locating a plurality of confocal targets that are distributed across the first swath, (ii) obtaining a focus setting for each confocal target, and (iii) constructing the initial focus trajectory based on an interpolation process on the focus settings obtained for the confocal targets. In another implementation, each z offset measurement vector specifies a plurality of focus errors with respect to the initial focus trajectory and a specific one of the identically designed areas of the first swath. In yet another embodiment, the identically designed area are dies and each z offset measurement vector for each die specifies a plurality of z offsets between the initial focus trajectory and a measured surface of the first swath at a plurality of die positions as determined from the autofocus data for such die positions. In a further aspect, the corrected z offset vector is constructed by (i) for each same die position of the dies, determining an average of a plurality of z offset measurements from the z offset measurement vectors for all the dies at such same die position; (ii) forming a corrected z offset vector portion for each die from the determined average z offset values for each same die position for such die; (iii) concatenating the corrected z offset vector portion for each die together; and (iv) adding an interpolated portion between each pair of concatenated corrected z offset vector portions, wherein each interpolated portion corresponds to each street area between each pair of dies and is based on an interpolation process being performed with respect to the concatenated corrected z offset vector portions. In a further aspect, one of the interpolated portions is prepended to the concatenated corrected z offset vector and interpolation portions.

In a further embodiment, the identically designed areas are dies, and the method further includes (i) using the inspection tool to scan the first swath at the corrected z offset vector to collect inspection image data; and (ii) performing a die-to-die inspection analysis on the collected inspection image data to detect defects. In a further aspect, second autofocus data is also collected during the scan of the first swath at the corrected z offset vector, and the method further comprises (i) repeating the operation for generating a z offset measurement vector for each identically designed of a next swath based on the second autofocus data and (ii) repeating the operation of constructing a corrected z offset vector for the next swath.

In an alternative embodiment, the invention pertains to an inspection system for detecting defects in a semiconductor sample having a plurality of identically designed areas. The system includes at least one memory and at least one processor that are configured to perform any combination of the above-described operations.

These and other aspects of the invention are described further below with reference to the figures.

DETAILED DESCRIPTION OF EXAMPLE EMBODIMENTS

Figure 1:
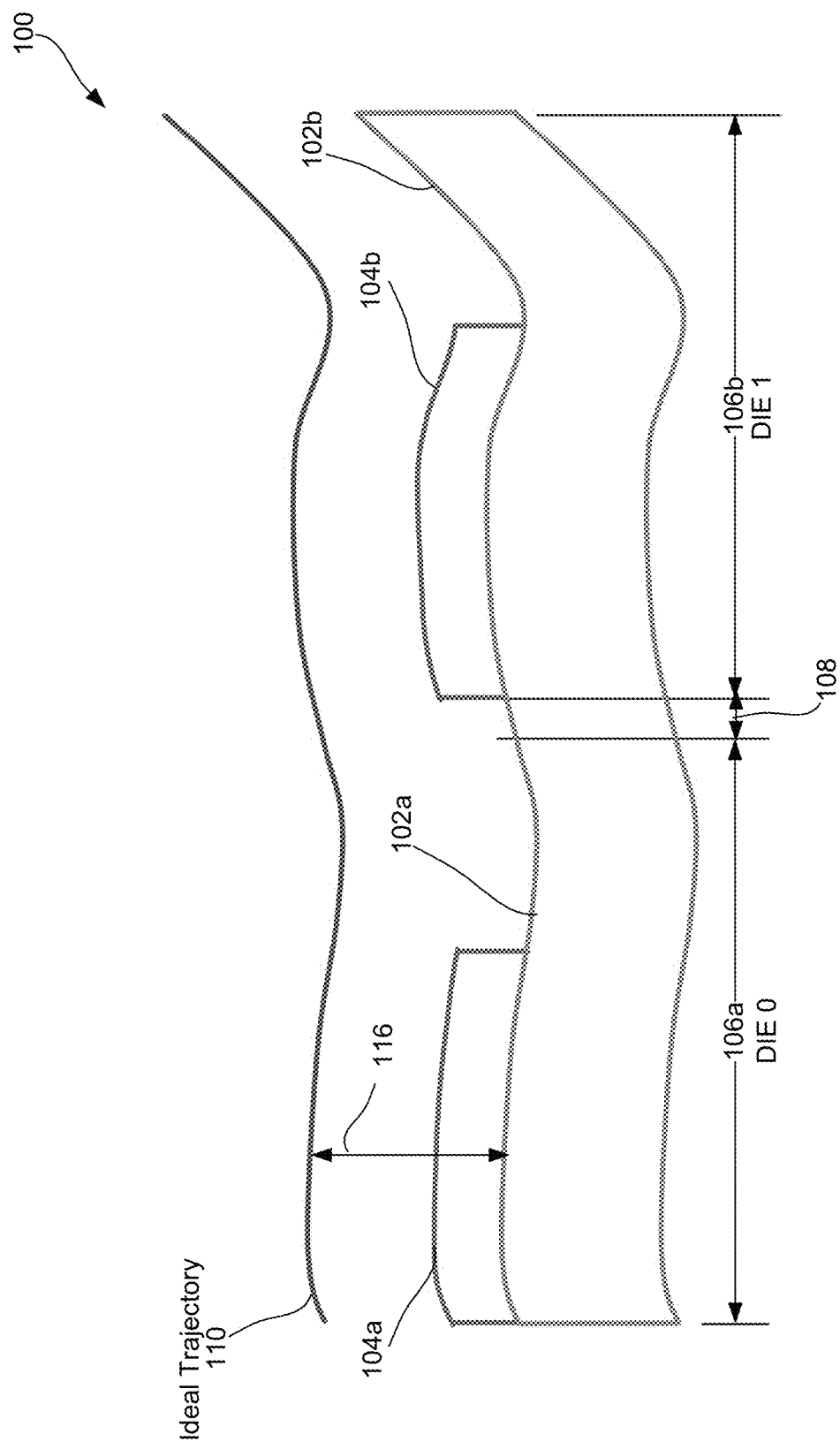
FIG. 1 is a side view of a simplified reticle portion.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

The inspection techniques described herein may be implemented with respect to any suitable specimen having areas that are designed to be identical. One example specimen is a semiconductor reticle having multiple dies or cell arrays that are designed to be identical. Specimens can also take the form of a semiconductor wafer, a solar panel, a computer disk, etc.

An integrated circuit wafer with multiple device dies is typically fabricated from a plurality of reticles having multiple device dies. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication process.

After fabrication of each reticle or group of reticles, each reticle is typically inspected by illuminating it with light emanating from a controlled illuminator. A test image of a portion of the reticle is constructed based on the portion of the light reflected, transmitted, or otherwise directed to a light sensor. Such inspection techniques and apparatus are well known in the art and are embodied in various commercial products such as many of those available from KLA-Tencor Corporation of Milpitas, Calif.

During a conventional inspection process, the test image of the reticle is typically compared to a baseline image. Typically, the baseline image is either generated from the circuit pattern data or from an adjacent die on the reticle itself. Either way, the test image features are analyzed and compared with features of the baseline image. Each difference value is then compared with a predetermined threshold value. If the test image varies from the baseline image by more than the predetermined threshold, a defect is defined and reported.

Certain semiconductor inspection modes are based on the comparison of features on the sample that are designed to be identical. Resulting anomalies from the comparison results may be identified as defect candidates. For instance, die-to-die inspection includes comparing two dies that are designed to be identical. Cell-to-cell inspection includes comparing two cells that are designed to be identical. Each difference detected between two images has the potential of resulting in a printable defect. Conversely, some of the detected defects will have no effect on the resulting integrated circuit and can, thus, be considered "false" defects.

Die-to-die inspection results may often be affected by the level of relative focus or defocus differences between the same die or cell areas that are being inspected and compared. For instance, two corresponding, but unequally focused die portions from two dies may result in detection of false defects or failure to detect real defects in such unequally focused die portions.

FIG. 1 is a side view of a simplified reticle portion 100 having two die areas 106a and 106b separated by a street region 108. As shown, the reticle portion 100 includes pattern portions 104a and 104b for dies 106a and 106b, respectively. The pattern portions of each die would contain varying density and configurations of design structures. Each die would typically include multiple pattern portions although not shown in FIG. 1 so as to simplify the description. Each die 106a and 106b would also include blank mask areas, such as 102a and 102b, respectively.

When images are obtained from multiple dies during an inspection scan of the reticle, various techniques may be utilized to provide as accurate focus settings for scanning across the reticle while minimizing the focus error between the dies. Optimum focus settings (or z offset settings) would generally entail that each position of the specimen surface is optimally focused as the inspection tool scans across the specimen. Terms relating to a "z offset" and "focus" are used interchangeably herein.

Relative die-to-die focus error may be defined as the difference in focus at locations in one die versus focus at the same location of another die, in a die-to-die inspection. This focus error difference between the focus at the same positions of multiple dies is preferably eliminated or at least minimized.

In the illustrated example, an ideal focus trajectory 110 (also without focus error) would map an ideal focus offset 116 of the inspection objective with respect to the mask surface of the reticle portion 100. That is, the z offset between the objective and the specimen surface would remain constant at an optimum focus as the objective is moved relative to different topographies of the specimen surface so that the specimen surface would be in focus. For example, the mask surface topography may not be completely flat and may vary due to bowing or unevenness. The ideal focus trajectory may represent an optimum focus for any suitable surface of the specimen, such as the mask surface as illustrated or the various topmost surface areas, such as surfaces of the pattern portions 104a and 104b and blank mask portions 102a and 102b.

There are various techniques for performing autofocus for an inspection process. One autofocus technique includes using focus sensors to measure distance between the objective lens and the reticle surface at every x,y location (e.g., using a triangulation approach to determine defocus), and to attempt to adjust the measured distance so as to maintain an optimum focus distance using an automatic control system. An advantage of this method is that the focus sensors tend to sense corresponding places in each die in the same way—or phrased in another way, with common-mode errors—so that relative die-to-die errors would be conceptually held to zero if the control system for adjusting focus provided perfect response.

However, perfect response is not achievable in practice using focus sensors with a focus adjustment control system for several reasons. Although the focus sensors give nominally the same reading at corresponding x,y locations within each die, the focus sensors do not generally provide the same readings before and after each die. This discrepancy occurs because the first die seen in an inspection swath usually is preceded by a wide area of uniform material, and subsequent die are preceded by generally much narrower "die streets", which are not generally of uniform material, and may be different in terms of material and material pattern from each other. Presented with these different sensor readings outside of the die, the finite speed of response of the control system to adjust the focus setting will tend to result in large relative focus errors. Another disadvantage of this method is that absolute focus accuracy is generally poor. This is true first because focus sensors are generally subject to an error called "pattern effect", in which the apparent height of a patterned reticle surface is changed by optical diffraction interaction between the focus sensor light and the fine-pitch patterns on the reticle surface.

Another autofocus technique is to employ various measurement techniques of a specimen to construct absolute focus trajectories that track the apparent topographic surface of the specimen as described in U.S. Pat. No. 7,835,015, which patent is incorporated herein by reference as providing techniques that may be enhanced by embodiments of the present invention as further described below. An absolute trajectory may be formed, for example, from interpolation of measurements obtained from specific confocal targets having relatively large areas of uniform intensity that are located across or near the reticle inspection area. Other techniques for constructing an absolute focus trajectory are further described in U.S. Pat. No. 7,835,015. Alternatively, construction of an absolute trajectory can include obtaining and using various triangulation measurements to determine the surface distance from the objective.

An inspection of the specimen can then be performed as the focus setting tracks the determined absolute focus trajectories. These absolute trajectory techniques can generally provide good absolute focus performance, but are not "informed" in any way by knowledge of the repeating nature of a die-to-die inspection. Errors in absolute focus result in errors in die-to-die relative errors.

Certain embodiments of the present invention provide improved relative die-to-die focus settings, as compared to autofocus techniques that do not account for relative die position information. In general, focus trajectory settings at corresponding die locations are adjusted with respect to each other to minimize the relative die focus error.

Figure 2:
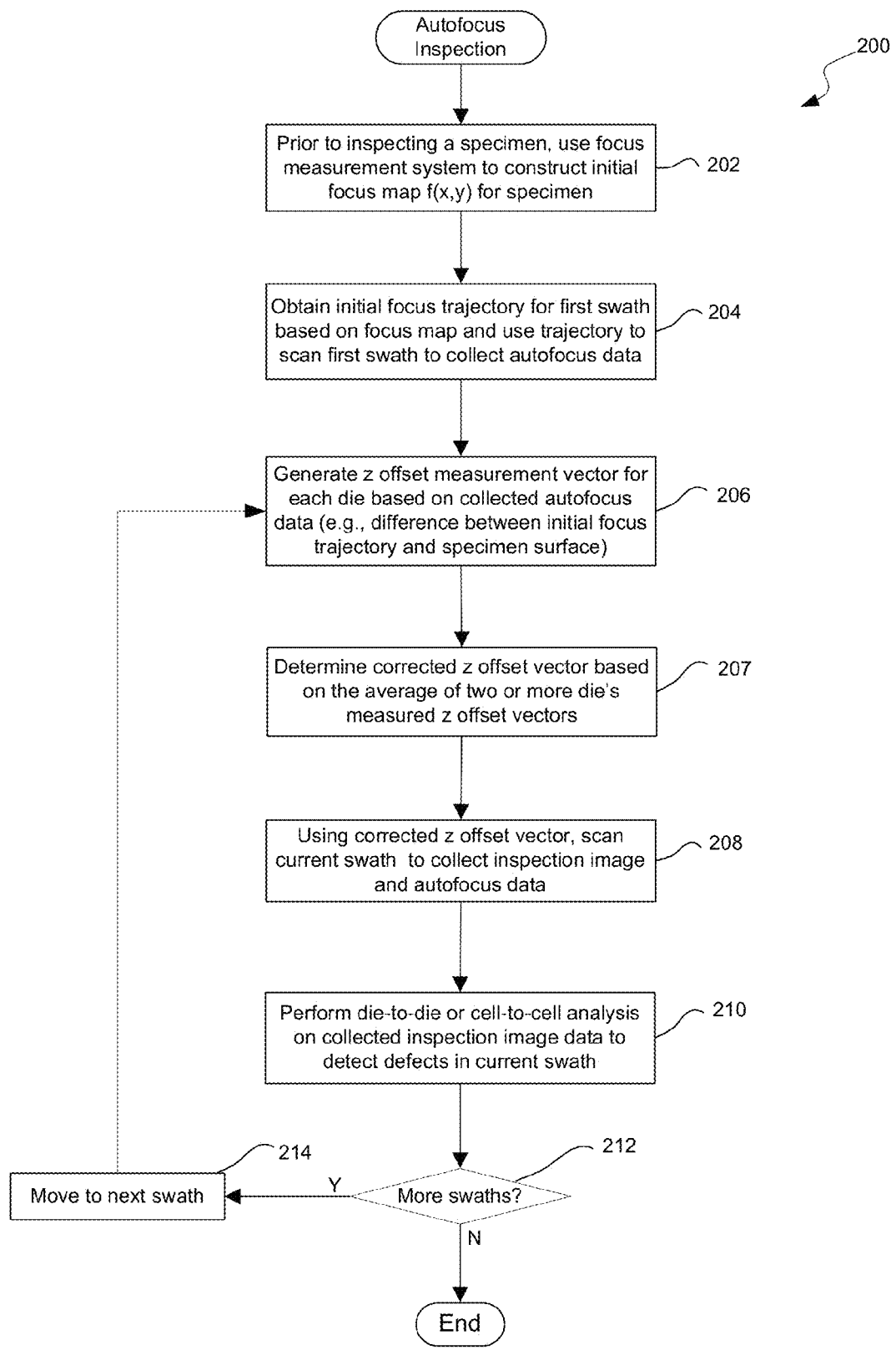
FIG. 2 is a flow chart illustrating an autofocus inspection procedure in accordance with one embodiment of the present invention.

FIG. 2 is a flow chart illustrating an autofocus inspection procedure 200 in accordance with one embodiment of the present invention. Initially, prior to inspecting a specimen (e.g., a reticle), a focus measurement system (e.g., of an inspection system) may be used to construct an initial focus map, f(x,y), for the specimen surface in operation 202. The focus map generally specifies tracking of a focus offset (z) relative to specimen surface x,y positions.

The initial focus map may be based on individual focus trajectories, where each trajectory is a function of a first dimension and obtained for a particular second dimension. For instance, f(x) is obtained for each particular y position. The focus trajectories are generally obtained for a plurality of "map swaths" that are distributed across the specimen's active area. For instance, a reticle tends to have a central rectangular shaped active area. In one embodiment, the active area is generally divided into rectangular shaped map swaths from which image or other measurement data is obtained for constructing a focus trajectory for each swath.

Figure 3:
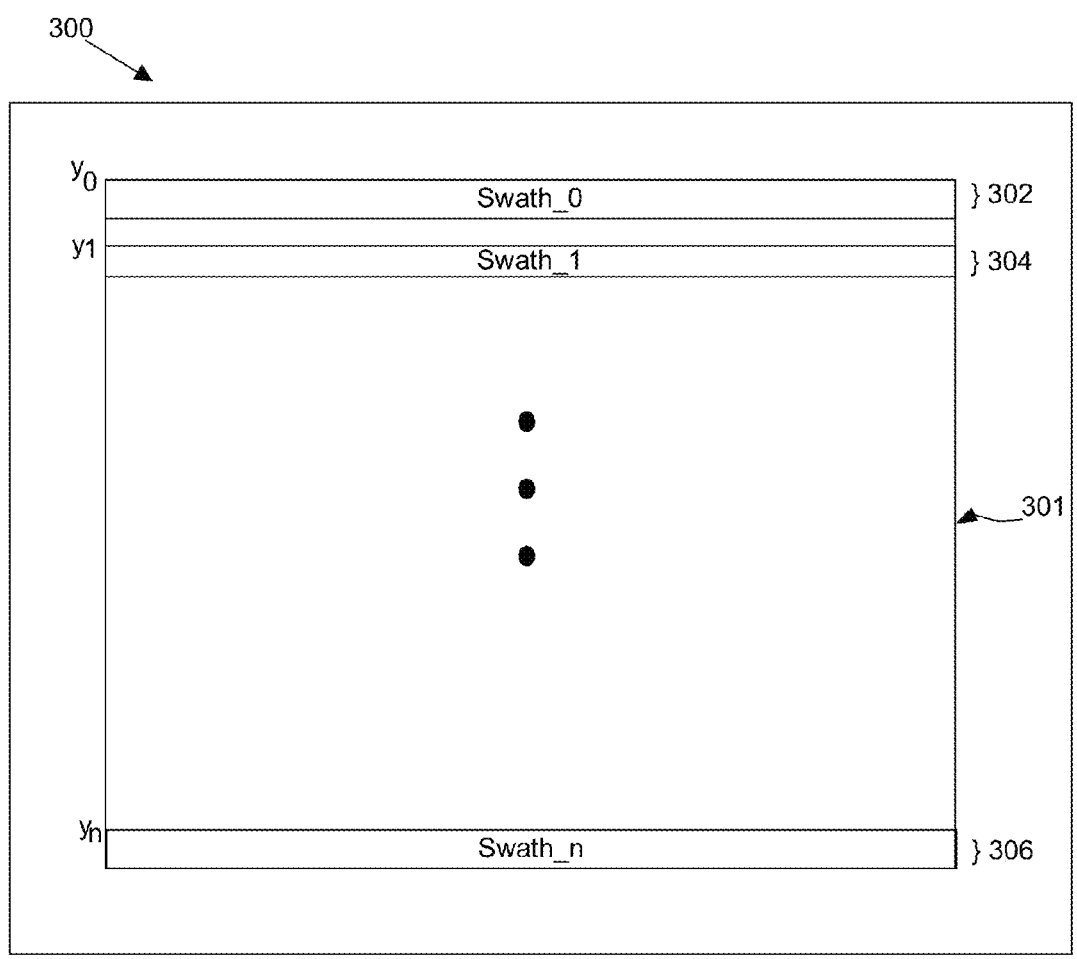
FIG. 3 is a diagrammatic representation of multiple inspection swaths of a sample, such as a reticle.

FIG. 3 is a diagrammatic representation of multiple map swaths of an active area 301 of sample 300, such as a reticle. The sample may include multiple active areas of one or more shapes and sizes although only a single rectangular active area 301 is illustrated in FIG. 3. The maps swaths may also encompass areas outside the regions to be inspected.

Image data may be collected for each map swath of the sample 300. For example, a first set of image data corresponds to a first swath 302 of the sample 300, and a second set of image data corresponds to a second swath 304 of the sample 300. As shown, the active area 301 may include a plurality of swaths, e.g., swath_0 (302) to swath_n (306).

Each set of image data may be obtained by sequentially scanning swaths from the sample in a serpentine or raster pattern. For example, the first swath 302 of the sample 300 is scanned by an image acquisition system from left to right to obtain a first set of image data. The second swath 304 is then scanned from right to left to obtain a second set of image data. Swaths of image data may be sequentially scanned until a last swath 306 is reached. In one example, the map swaths are about 10 mm apart for an inspection area of about 100 mm so that 11 map swaths of image data are obtained for the inspection area. Swath size and count can vary, depending on the particular specimen's inspection area configuration and the desired absolute focus variance or desired accuracy.

Figure 4:
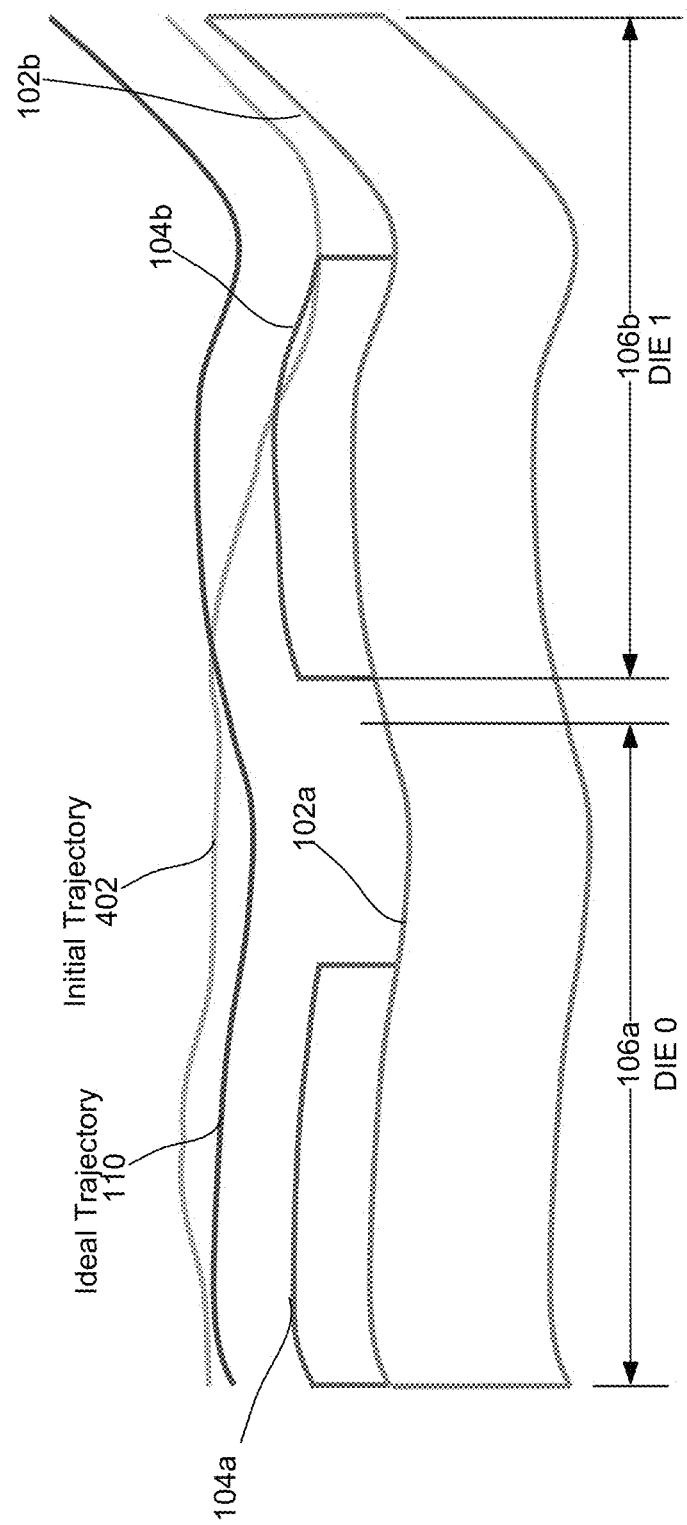
FIG. 4 illustrates an example initial focus trajectory that is constructed for the reticle portion of FIG. 1.

In this example, each map swath corresponds to different y positions. In this embodiment, each map swath is positioned at a particular y position. For instance, swath_0 302 corresponds to $y_0$; swath_1 304 corresponds to $y_1$; and swath_n corresponds to $y_n$. For each y position and swath, an initial focus trajectory may be calculated based on the image data for such swath. That is, an initial focus offset position trajectory or z(x) for each y swath position may be constructed. FIG. 4 illustrates an example initial trajectory 402 that is constructed for the reticle portion of FIG. 1.

Each focus trajectory may be determined by any number and type of autofocus techniques. For instance, initial trajectories may be obtained based on an initial focus map that is constructed by performing any of the techniques described in the above-referenced U.S. Pat. No. 7,835,015. Several techniques may be combined to construct an initial focus map.

One technique for determining a trajectory for a particular map swath includes first gathering image data for the particular map swath to look for relatively uniform areas of intensity. Such uniform areas are referred to as "confocal targets" and are preferably found at regular intervals (e.g., at a frequency of at least about every 10 mm) across the width of the map swath.

For each confocal target, the inspection system may then be used as a confocal measurement system to gather intensity data for such confocal targets at different focus settings. The collected intensity data may then be analyzed to determine an optimum focus (or z position) for each confocal target. For instance, the focus position for a confocal target that results in the most collected light through a pin hole located at an intermediate field plane is determined to be the optimum focus offset for such confocal target position.

Figure 5:
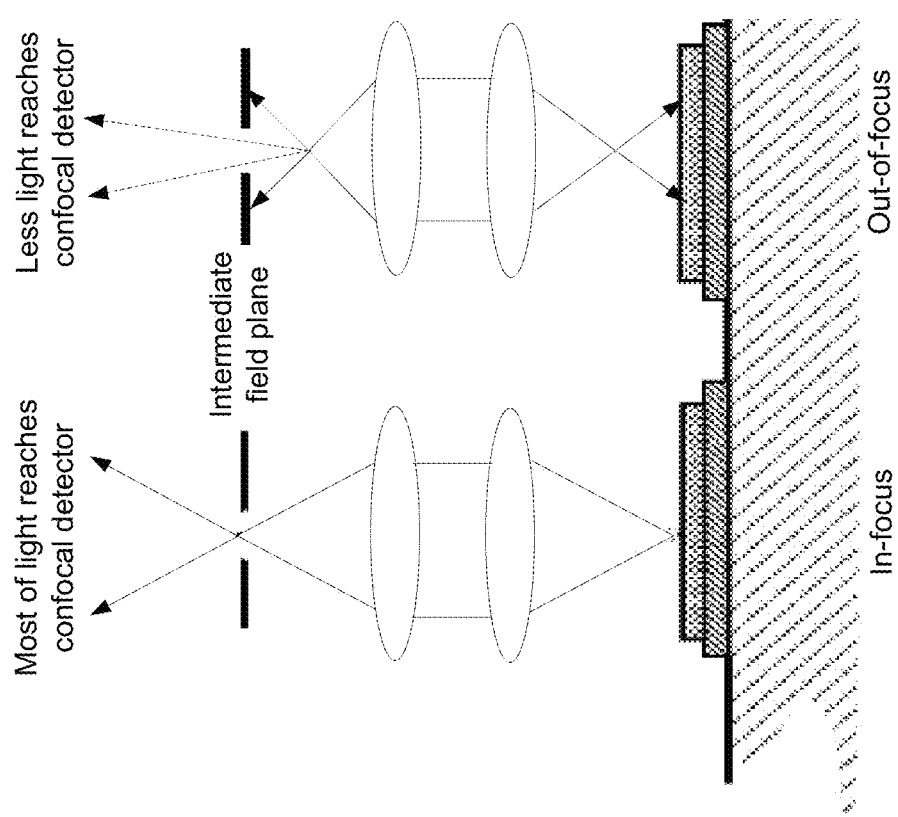
FIG. 5 illustrates determination of focus for confocal targets using pin-hole.

By way of example, a diffraction-limited pin-hole may be located at the back focal plane of the objective lens, and such pin-hole may be illuminated to project a spot onto the reticle. The reflected light image of this spot may then be re-imaged onto the original pin-hole. When the objective-to-reticle distance is at best focus, the maximum amount of reflected light will pass through the pin-hole as illustrated in FIG. 5. Various methods of identifying the best locations may be used for this confocal target approach and a mask-material table may document the thickness and reflectivity of each material to assist in identifying the best locations.

Figure 6:
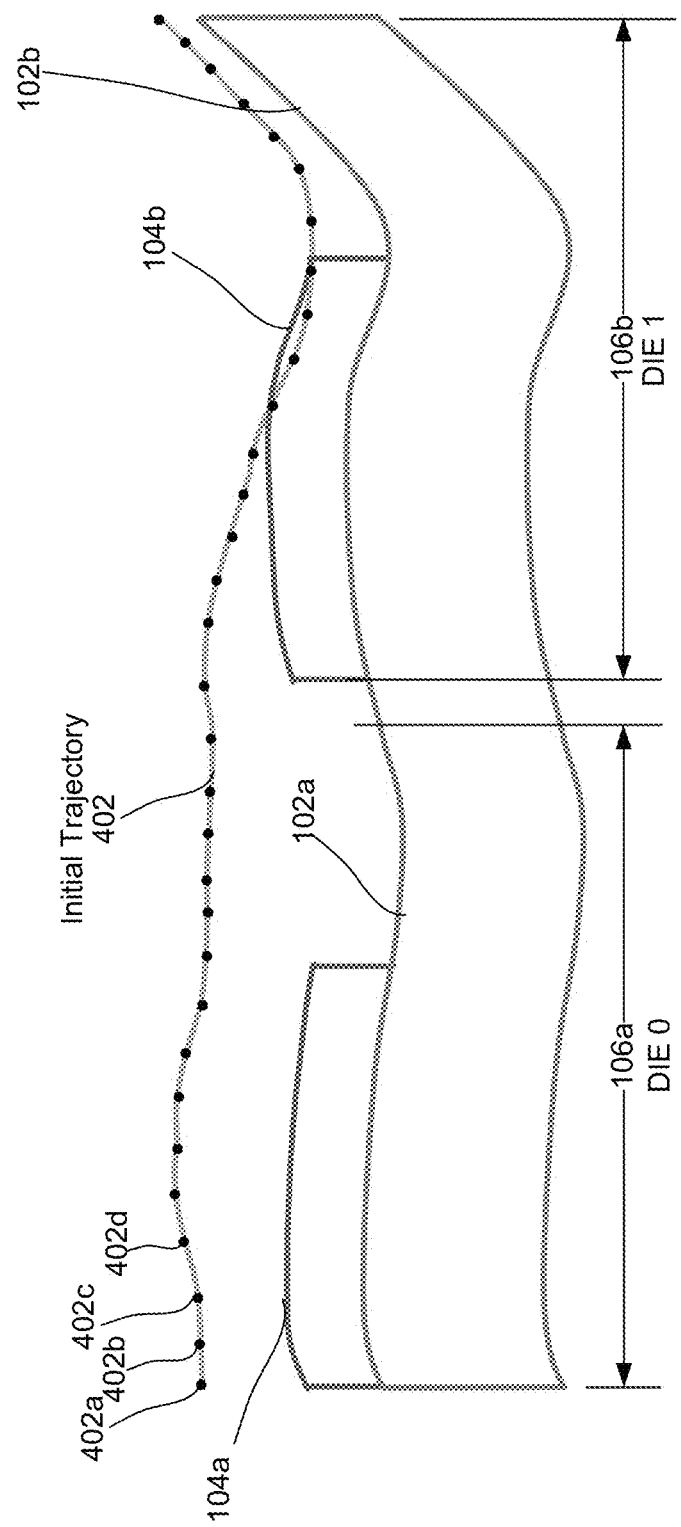
FIG. 6 illustrates construction of an initial focus trajectory from a plurality of optimum focus positions that were determined for confocal targets.

The optimum determined focus positions for the confocal targets can then be analyzed to interpolate a complete z(x) trajectory for the particular y position. FIG. 6 illustrates construction of initial focus trajectory 402 from a plurality of optimum focus positions (e.g., 402a~402d) that were obtained for confocal targets at a particular y position, such as $y_0$. Similar techniques may be used to construct multiple initial focus trajectories at multiple y positions, such as $y_1$~$y_{10}$. For example, a linear interpolation may be used to construct each initial focus trajectory from optimum z positions measured from specified confocal targets. In this example, a focus trajectory z(x) is obtained for 11 different y positions.

Although an initial focus trajectory may be accurate for some areas of the sample, the focus trajectory may be inaccurately determined for other areas of the samples, such as densely patterned areas. For areas in which a good uniform intensity target cannot be found, the process may locate a least bad confocal target if a relatively uniform area cannot be found within a predefined interval of x, for example. Such "least bad" confocal targets may be in the form of a dense pattern and may, accordingly, diffract the autofocus light such that optimum focus is inaccurately determined for such patterned confocal targets. These absolute autofocus errors may also vary from die to die to result in relative die-to-die autofocus errors.

An initial focus trajectory for a first swath may be obtained based on the initial focus map and such trajectory used to scan the first swath to collect autofocus data in operation 204. For instance, the z(x) trajectory from the initial focus map that corresponds to the first swath's y position is used to position the objective relative to the sample at sequential x positions as the first swath is scanned to collect autofocus data. If the first swath's y position is not the same as any of the y positions for the initial focus map trajectories, an initial focus trajectory may be interpolated for the first swath's y position. In one example implementation, an initial focus trajectory for the first swath's y position that is between $y_0$ and $y_1$ is interpolated from the two trajectories for $y_0$ and $y_1$. For example, if the first swath's y position is exactly half way between $y_0$ and $y_1$, an initial trajectory having values that are half way between the initial trajectory values of $y_0$ and $y_1$ can be used as the initial focus trajectory for the first swath.

A z offset measurement vector for each die may be generated based on the collected autofocus data in operation 206. The z offset measurement vector generally specifies an apparent focus error (or defocus error) measurement with respect to the initial trajectory for each die position. In one embodiment, the z offset measurement vector specifies a difference between the initial focus trajectory and the specimen's apparent surface for die position. Autofocus data may include any suitable measurement data that can be used to determine or estimate a focus error of the initial trajectories. In one embodiment, the autofocus data includes triangulation autofocus data. In other embodiments, the autofocus data may also include focus error determined by analysis of the inspection image data, etc.

In a triangulation approach, two counter-propagating, off-axis beams may be focused onto the same spot on the surface of the sample as the initial focus trajectory is followed. For instance, their reflected images may be directed onto two different sensors or sensor partitions (e.g., bi-cell or quad-cell photodiode detectors, linear CCD arrays, position-sensitive detectors, etc.) so that any defocus of the reticle results in equal-but-opposite displacements of the spots on the two detectors. The measurement of the surface's apparent position with respect to the initial z offset trajectory may be determined by normalizing and analyzing the difference signals (e.g., the current signals) for the two detectors.

Figure 7:
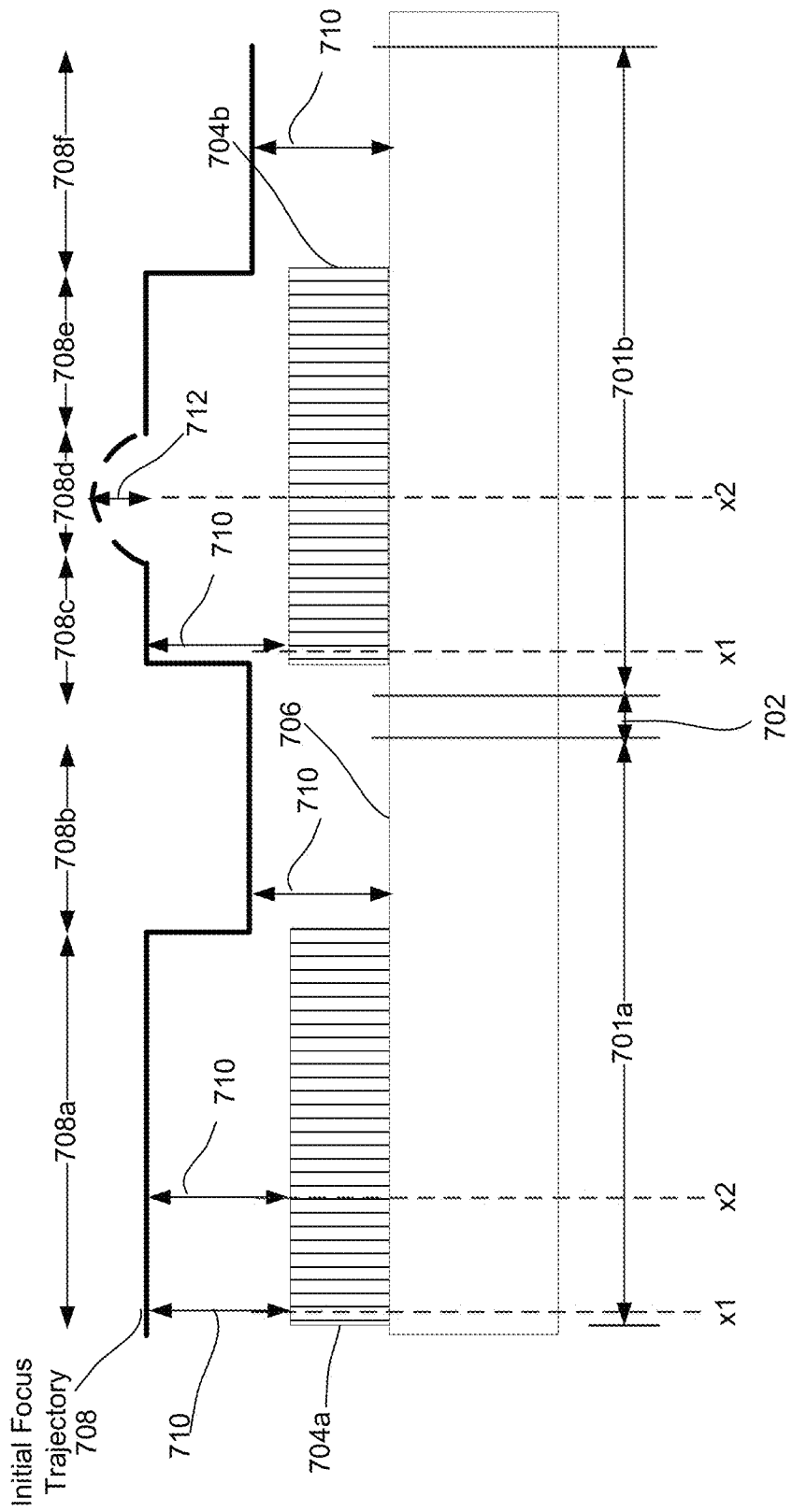
FIG. 7 illustrates a simplified example of generation of a z offset measurement vector in accordance with one embodiment of the present invention.

FIG. 7 illustrates a simplified example of generation of a z offset measurement vector in accordance with one embodiment of the present invention. As shown, an initial focus trajectory 708 has substantially optimum focus offset with minimal die-to-die focus errors. That is, initial focus trajectory 708 results in most die positions being at optimum focus with only a small area in one of the dies being defocused. That is, this example initial focus trajectory 708 has an optimum constant focus distance z offset 710 from the surface, except at discrepancy area 708d. Specifically, pattern portion 708a and unpatterned portion 708b of die 701a have ideal focus offset 710, and pattern portions 708c and 708e and unpatterned portion 708f for die 701b also have ideal focus offset 710. However, pattern portion 708d of die 701b has different defocused offsets. For instance, position x2 is associated with a maximum focus error 712, which is the difference between the ideal focus offset 710 and the defocused offset.

The example initial focus trajectory 708 of FIG. 7 would result in most of the same die-to-die positions having the same focus setting and being free of die-to-die focus errors. For instance, the focus offset of the same relative die position x1 for both die 701a and 701b has the same value 710. However, this same initial focus trajectory 708 results in the same die-to-die position x2 having different focus error measurements (e.g., one focused and one defocused), which will likely adversely affect a die-to-die inspection of the corresponding dies 701a and 701b if left uncorrected.

Figure 8:
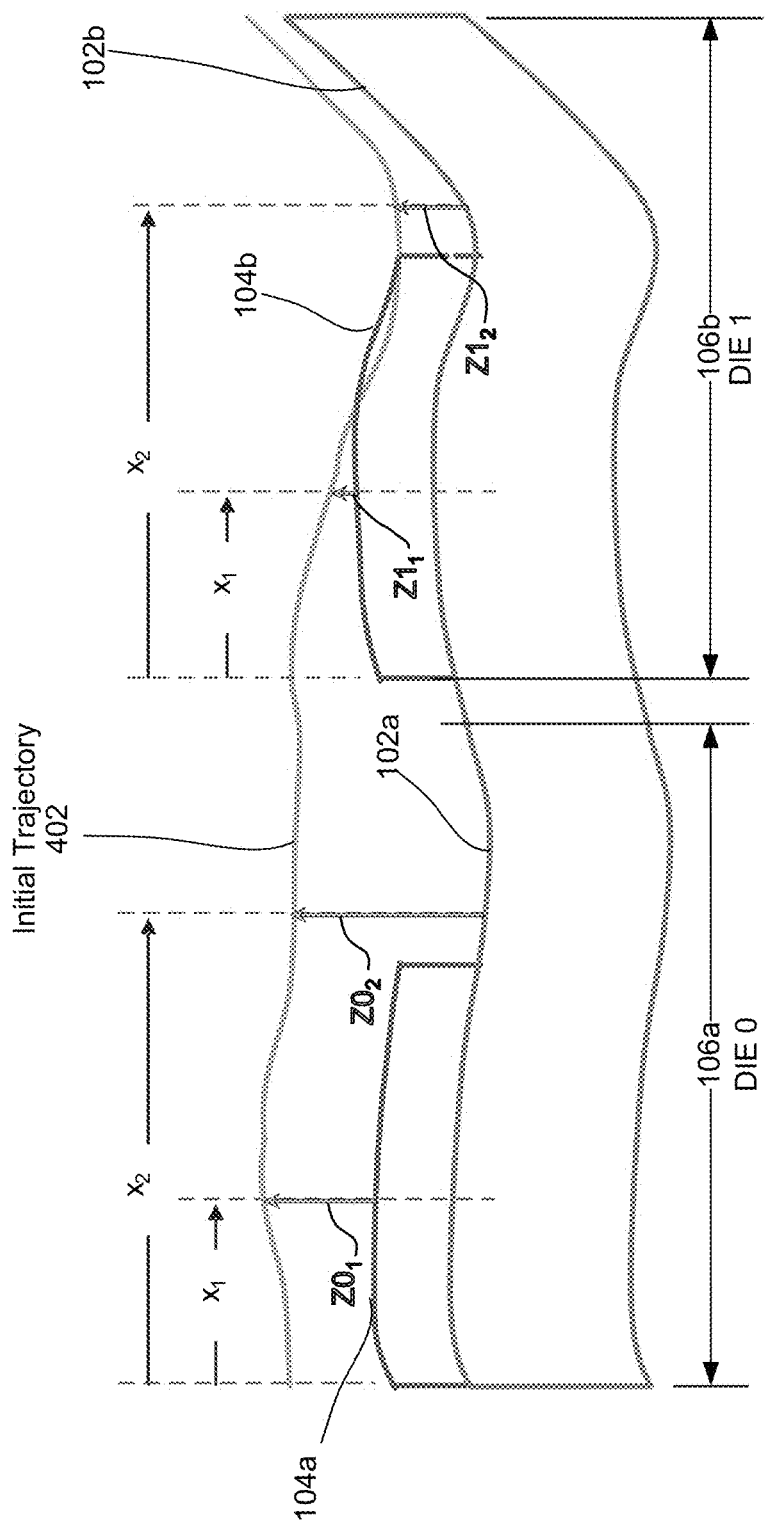
FIG. 8 illustrates focus error measurements for the initial trajectory of FIGS. 4 and 6.

Although the simplified initial focus trajectory of FIG. 7 shows only one example of die-to-die focus error, a typical reticle (or other sample) of fine pattern structures would typically result in a significant number of die-to-die focus errors. FIG. 8 illustrates the focus error measurements for the non-ideal initial trajectory 402 of FIGS. 4 and 6. As shown, position x1 for die_0 106a has focus measurement $Z0_1$, which differs from the corresponding focus measurement $Z1_1$ for position x1 for die_1 106b. Likewise, position x2 for die_0 106a has focus measurement $Z0_2$, which differs from the corresponding focus measurement $Z1_2$ for position x2 for die_1 106b.

Certain embodiments of the present invention generate a corrected focus trajectory that results in the same relative die-to-die positions having either the same optimum focus or the same defocus setting. In the illustrated embodiment, the measured z offset vector may be used to determine a corrected z offset vector in operation 208. The corrected z offset vector generally specifies differences between the initial focus trajectory and the apparent surface at each position of the first swath.

The discrepancies for the initial focus trajectory can be managed by combining the autofocus data for the same die positions to generate a corrected z offset vector. Two or more z offset measurements for each particular die position can be combined in any suitable manner so that the resulting z offset is the same value for the two or more die positions. Referring to the illustrated embodiment of FIG. 2, a corrected z offset vector may be determined based on the average of two or more die's measured z offset vectors in operation 207.

Figure 9:
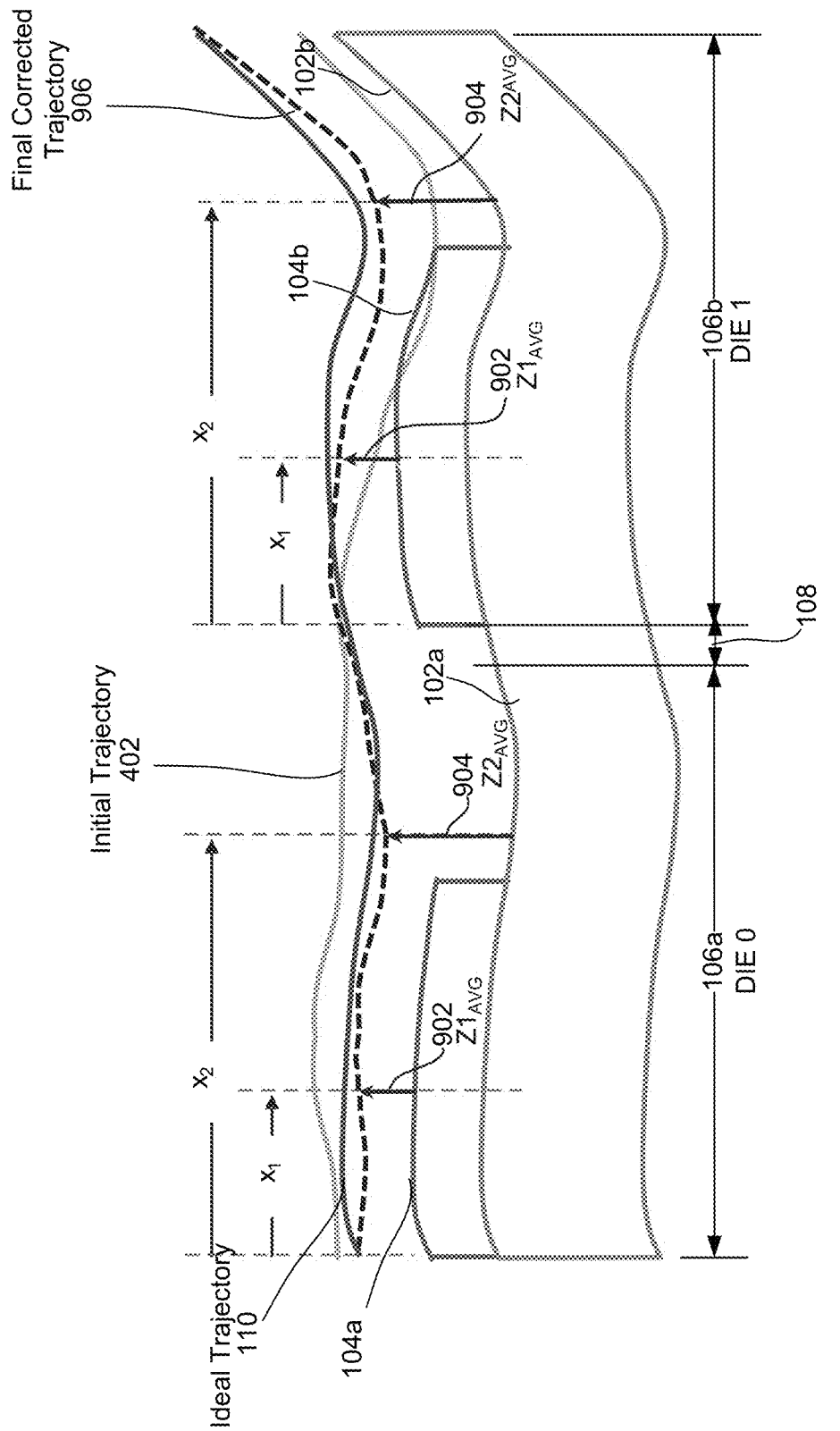
FIG. 9 illustrates construction of a final corrected z offset vector for each die based on average z offsets measurements in accordance with one implementation of the present invention.

FIG. 9 illustrates construction of a final corrected z offset vector for each die based on average z offset measurements in accordance with one implementation of the present invention. As shown, the average measured z offset value $Z1_{avg}$ (902) for die position x1 in both dies 106a and 106b is equal to $(Z0_1+Z1_1)/2$ (from FIG. 8), and the average measured z offset value $Z2_{avg}$ (904) for die position x2 in both dies is equal to $(Z0_2+Z1_2)/2$ (from FIG. 8). Average measured z offset values may similarly be determined for each die position in both dies. Although the averaging of only two dies' measured z offset values is shown, averages may be determined for any portion or all of the dies of a particular sample.

A corrected z offset vector for each die may then be constructed from the average measured z offset values for each die. In one specific embodiment, a vector of offsets Zcorrection(x) is created for each die which, when added to the initial focus offset trajectory (from 202), will cause each die to have the same focus sensor measurement at each die position within the die. For the ith die, $Zfinal_i(x)$ can equal $Zmap_i(x)+Zcorrection_i(x)$.

The corrected z offset vectors for each die are separated by die streets, which may vary from each other. The die streets can vary significantly (e.g., only some streets having test targets). It may be desirable to facilitate the servo positioning mechanisms that set the z offset to not have to handle abrupt changes. Certain embodiments of the present invention may include concatenating the corrected z offset vectors for each die together while minimizing z offset movement in the street areas to form a complete swath's final corrected z offset vector 906. For example, extra-die and inter-die discontinuities may be removed by performing any suitable curve fitting or interpolation process, such as an extrapolation and/or spline interpolation, between the corrected z vectors to form the street portions (e.g., 108) of the final corrected z offset vector 906. As a result, the sample's street areas are ignored when forming the final corrected z offset vector. An interpolated portion of the final trajectory that precedes a die that is positioned after the first die may also be pre-pended before the first die in the swath. The edge street portions that are adjacent to dies may also be altered to be similar or identical to each other. For example, an average edge portion can be constructed.

Although the techniques described herein are described in relation to identically designed dies, they may alternatively be applied to any identically designed areas of a specimen, such as cell arrays. Additionally, although the same corrected z offset is described herein as being calculated for the same die positions in the same swath, the same corrected z offset can also be calculated for the same die positions that are located in different swaths under certain conditions. For example, a first set of swaths may cover a first set of identical dies, and a second set of swaths cover a second set of identical dies that are identical to the first set of dies. This intra-swath die-to-die focus technique may generally include storing corrected focus setting for each particular die position. When a new set of dies is reached by a swath scan, then the stored corrected focus settings for the same die positions can be used.

The first swath's final corrected z offset vector may then be used to inspect the first swath for defects. For instance, using the final corrected z offset vector, the current swath may be scanned to collect inspection image data and autofocus data in operation 208. A die-to-die or cell-to-cell inspection analysis may then be performed on the collected inspection image data to detect defects in the current swath in operation 210.

It may then be determined whether there are any more swaths to inspect in operation 212. If there are no more swaths, the autofocus inspection procedure may then end. Otherwise, the procedure may move to the next swath in operation 214. For instance, the inspection tool scans to the beginning of the next swath. New z offset measurement vectors for each die may then be generated based on the autofocus data that was collected for the first swath in operation 206. The remaining operations may then be repeated for the current swath to generate a new final corrected z offset vector Subsequent measurement vectors will typically have smaller relative die-to-die focus errors since such subsequently determined vectors are based on autofocus data from a previously corrected swath and adjacent swaths tend to have the same focus requirements. These operations 206 through 214 may be repeated for each subsequent swath.

Certain techniques of the present invention may implement various mechanisms for identifying same die positions among multiple dies. In one implementation, specific die positions can be determined with respect to one or more origin marks on the sample, such as a cross-shaped mark that provides an xy origin. Each die's boundaries or origin position with respect to such xy origin may be known, for example, by specification in the sample design data. Each dies' other positions can then be known or determined with respect to such die's origin. Each set of identical dies can then have a set of xy die positions relative to a die origin.

Certain techniques of the present invention result in the same relative trajectories for the same relative die positions, which can result in a reduction in the detection of false defects caused by die-to-die focus errors. That is, certain embodiments provide a way of matching Z trajectories among all die in a die-to-die inspection, theoretically reducing relative die-to-die errors to a level limited only by sensor noise level and finite servo response. Further, averaging the measurements among multiple die may reduce the effect of sensor noise. Also, certain embodiments improve absolute focus by averaging the Z trajectory among all the die—thereby reducing the maximum absolute focus errors in individual die. These methods may have negligible effect on inspection throughput-requiring only a single added swath prior to the inspection to start the process.

In an alternative approach, correction vectors may be averaged over two or more swaths preceding the current inspection swath. In another embodiment for inspections that are expected to be benign in terms of absolute focus error, an initial Z(x,y) map does not need to be created. The first swath may be scanned to determine focus or defocus measurements at a particular z offset setting and then the process may include averaging focus measurements among all the die. In this implementation, the correct absolute focus offset may be inferred from knowledge of the materials on the borders of the active area and knowledge of the thickness of these materials. Knowing the apparent height of these materials on the borders (measured accurately by the autofocus sensors because the materials are not patterned at the borders), allows post-calculation of the absolute height to follow, rather than just having the servo follow the height measured in the active area which is typically subject to large errors due to pattern effect. Additionally, the servo response when scanning from one of these blank materials into a patterned area is usually subject to the limitation of the finite servo bandwidth, and the response to the "step" transient encountered at this boundary would necessarily have transient error that takes a finite time to become small. Accordingly, this approach would result in avoiding this transient error problem. Pre-die and inter-die smooth trajectories may also be calculated in this approach as described above. This alternative approach would improve throughput by skipping the overhead time required for constructing an initial Z offset map.

Figure 10:
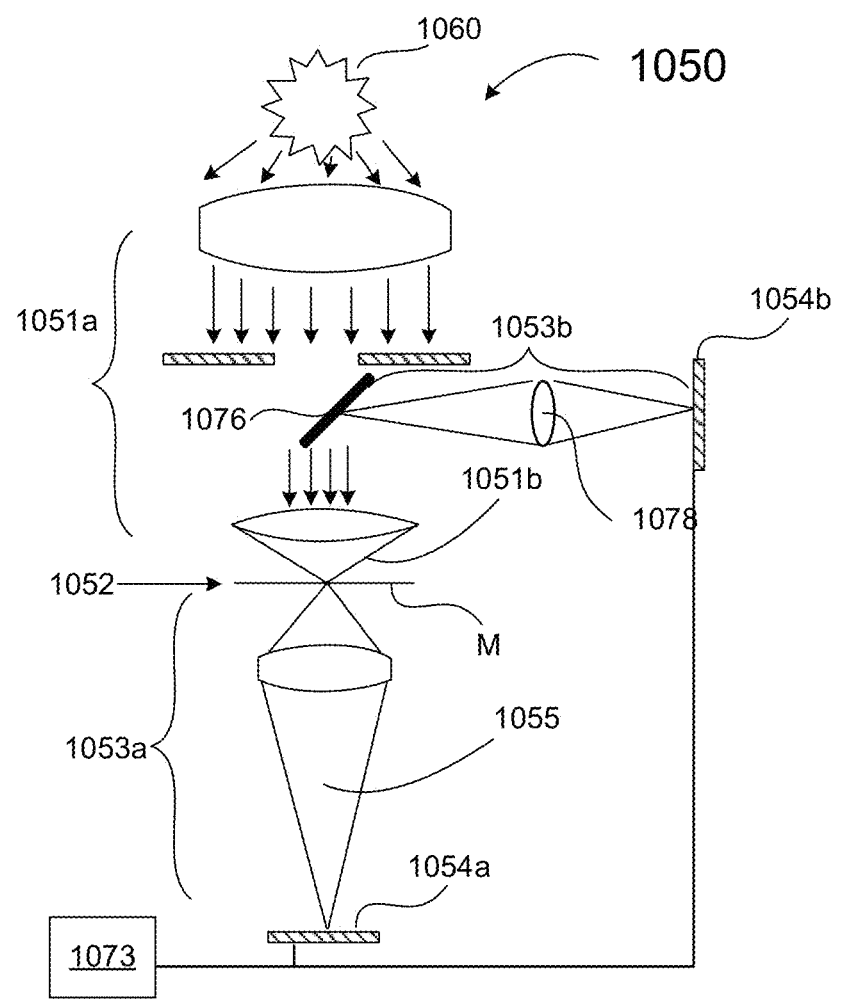
FIG. 10 provides a schematic representation of an inspection apparatus in accordance with certain embodiments.

FIG. 10 provides a schematic representation of an example inspection system 1050 that has illumination optics 1051a includes an imaging lens with a relative large numerical aperture 1051b at a reticle plane 1052 in accordance with certain embodiments. The depicted inspection system 1050 includes detection optics 1053a and 1053b, including microscopic magnification optics designed to provide, for example, 60-200× magnification or more for enhanced inspection. The detection optics may also include autofocus components, such as pin-holes.

The inspection techniques described herein may be implemented on various specially configured inspection systems, such as the one schematically illustrated in FIG. 10. The illustrated system 1050 includes an illumination source 1060 producing at least one light beam that is directed through illumination optics 1051a onto a photomask M in the reticle plane 1052. As explained above, the inspection system 1050 may have a numerical aperture 1051b at the reticle plane 1052 that may be greater than a reticle plane numerical aperture of the corresponding lithography system. The illumination optics 1051a may also include various lens and modules for achieving multiple beams with different characteristics, such as for performing autofocus. The photomask M to be inspected is placed on a mask stage at the reticle plane 1052 and exposed to the source.

The transmitted image from the mask M is directed through a collection of optical elements 1053a, which project the patterned image onto a sensor 1054a. Optical elements (e.g., beam splitter 1076 and detection lens 1078) are arranged to direct and capture the reflected light onto sensor 1054b. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 1054a and/or 1054b) can be processed by a computer system 1073 or, more generally, by one or more signal processing devices, which may each include an analog-to-digital converter configured to convert analog signals from each sensor into digital signals for processing. The computer system 1073 typically has one or more processors coupled to input/output ports, and one or more memories via appropriate buses or other communication mechanisms.

The computer system 1073 may also include one or more input devices (e.g., a keyboard, mouse, joystick) for providing user input, such as changing focus and other inspection recipe parameters. The computer system 1073 may also be connected to the stage for controlling, for example, a sample position (e.g., focusing and scanning) and connected to other inspection system components for controlling other inspection parameters and configurations of such inspection system components.

The computer system 1073 may be configured (e.g., with programming instructions) to provide a user interface (e.g., a computer screen) for displaying resultant intensity values, images, and other inspection results. The computer system 1073 may be configured to generate initial and final z offset trajectories, analyze intensity, autofocus measurements, and/or other characteristics of reflected and/or transmitted sensed light beam. The computer system 1073 may be configured (e.g., with programming instructions) to provide a user interface (e.g., on a computer screen) for displaying resultant intensity values, images, and other inspection characteristics. In certain embodiments, the computer system 1073 is configured to carry out inspection techniques detailed above.

Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the defect detection characteristic data may be obtained from a transmitted, reflected, or a combination output beam. Accordingly, the present embodiments are to be considered as illustrative and not restrictive, and the invention is not to be limited to the details given herein.

What is claimed is:

1. A method for detecting defects in a semiconductor sample having a plurality of identically designed areas, the method comprising:

using an inspection tool to construct an initial focus trajectory for a first swath of the sample;

using the inspection tool to scan the first swath by following the initial focus trajectory for the first swath while collecting autofocus data;

generating a z offset measurement vector for each identically designed area in the first swath based on the autofocus data; and constructing a corrected z offset vector for inspection of the first swath with the inspection tool, wherein constructing the corrected z offset vector is based on combining the z offset measurement vectors for two or more of the identically designed areas in the first swath so that the corrected z offset vector specifies a same z offset for each set of same positions in the two or more identically designed areas.

2. The method of claim 1, further comprising:

constructing an initial focus map that specifies z offsets for a plurality of swaths that are located at a plurality of different y positions of the sample, wherein the initial focus trajectory for the first swath is based on the initial focus map.

3. The method of claim 2, wherein the y positions of the swaths for which the initial focus map specifies z offsets do not include the first swath's y position, and wherein the initial focus trajectory for the first swath is constructed by interpolation between two initial focus trajectories, which have first and second y positions between which the swath's y position is located and that are specified by the initial focus map.

4. The method of claim 1, wherein the initial focus trajectory for the first swath is constructed by:

locating a plurality of confocal targets that are distributed across the first swath;

obtaining a focus setting for each confocal target; and constructing the initial focus trajectory based on an interpolation process on the focus settings obtained for the confocal targets.

5. The method of claim 1, wherein each z offset measurement vector specifies a plurality of focus errors with respect to the initial focus trajectory and a specific one of the identically designed areas of the first swath.

6. The method of claim 1, wherein the identically designed area are dies and each z offset measurement vector for each die specifies a plurality of z offsets between the initial focus trajectory and a measured surface of the first swath at a plurality of die positions as determined from the autofocus data for such die positions.

7. The method of claim 6, wherein the corrected z offset vector is constructed by:

for each same die position of the dies, determining an average of a plurality of z offset measurements from the z offset measurement vectors for all the dies at such same die position;

forming a corrected z offset vector portion for each die from the determined average z offset values for each same die position for such die;

concatenating the corrected z offset vector portion for each die together; and adding an interpolated portion between each pair of concatenated corrected z offset vector portions, wherein each interpolated portion corresponds to each street area between each pair of dies and is based on an interpolation process being performed with respect to the concatenated corrected z offset vector portions.

8. The method of claim 7, further comprising:

pre-pending one of the interpolated portions to the concatenated z offset vector and interpolation portions.

9. The method of claim 1, wherein the identically designed areas are dies, the method further comprising:

using the inspection tool to scan the first swath at the corrected z offset vector to collect inspection image data; and performing a die-to-die inspection analysis on the collected inspection image data to detect defects.

10. The method of claim 9, wherein second autofocus data is also collected during the scan of the first swath at the corrected z offset vector, the method further comprises:

repeating the operation for generating a z offset measurement vector for each identically designed of a next swath based on the second autofocus data; and repeating the operation of constructing a corrected z offset vector for the next swath.

11. An inspection system for detecting defects in a semiconductor sample having a plurality of identically designed areas, the system comprising at least one memory and at least one processor that are configured to perform the following operations:

using the inspection system to construct an initial focus trajectory for a first swath of the sample;

using the inspection system to scan the first swath by following the initial focus trajectory for the first swath while collecting autofocus data;

generating a z offset measurement vector for each identically designed area in the first swath based on the autofocus data; and constructing a corrected z offset vector for inspection of the first swath with the inspection tool, wherein constructing the corrected z offset vector is based on combining the z offset measurement vectors for two or more of the identically designed areas in the first swath so that the corrected z offset vector specifies a same z offset for each set of same positions in the two or more identically designed areas.

12. The inspection system of claim 11, wherein the at least one memory and at least one processor that are further configured for:

constructing an initial focus map that specifies z offsets for a plurality of swaths that are located at a plurality of different y positions of the sample, wherein the initial focus trajectory for the first swath is based on the initial focus map.

13. The inspection system of claim 12, wherein the y positions of the swaths for which the initial focus map specifies z offsets do not include the first swath's y position, and wherein the initial focus trajectory for the first swath is constructed by interpolation between two initial focus trajectories, which have first and second y positions between which the swath's y position is located and that are specified by the initial focus map.

14. The inspection system of claim 11, wherein the initial focus trajectory for the first swath is constructed by:

locating a plurality of confocal targets that are distributed across the first swath;

obtaining a focus setting for each confocal target; and constructing the initial focus trajectory based on an interpolation process on the focus settings obtained for the confocal targets.

15. The inspection system of claim 11, wherein each z offset measurement vector specifies a plurality of focus errors with respect to the initial focus trajectory and a specific one of the identically designed areas of the first swath.

16. The inspection system of claim 11, wherein the identically designed area are dies and each z offset measurement vector for each die specifies a plurality of z offsets between the initial focus trajectory and a measured surface of the first swath at a plurality of die positions as determined from the autofocus data for such die positions.

17. The inspection system of claim 16, wherein the corrected z offset vector is constructed by:
   for each same die position of the dies, determining an average of a plurality of z offset measurements from the z offset measurement vectors for all the dies at such same die position;
   forming a corrected z offset vector portion for each die from the determined average z offset values for each same die position for such die;
   concatenating the corrected z offset vector portion for each die together; and
   adding an interpolated portion between each pair of concatenated corrected z offset vector portions, wherein each interpolated portion corresponds to each street area between each pair of dies and is based on an interpolation process being performed with respect to the concatenated corrected z offset vector portions.

18. The inspection system of claim 17, wherein the at least one memory and at least one processor that are further configured for:
   pre-pending one of the interpolated portions to the concatenated z offset vector and interpolation portions.

19. The inspection system of claim 11, wherein the identically designed areas are dies, and wherein the at least one memory and at least one processor that are further configured for:
   using the inspection system to scan the first swath at the corrected z offset vector to collect inspection image data; and
   performing a die-to-die inspection analysis on the collected inspection image data to detect defects.

20. The inspection system of claim 19, wherein second autofocus data is also collected during the scan of the first swath at the corrected z offset vector, and wherein the at least one memory and at least one processor that are further configured for:
   repeating the operation for generating a z offset measurement vector for each identically designed of a next swath based on the second autofocus data; and
   repeating the operation of constructing a corrected z offset vector for the next swath.

* * * * *